United States Patent
Balestracci

(10) Patent No.: US 8,216,181 B2
(45) Date of Patent: Jul. 10, 2012

(54) APPARATUS AND METHODS FOR SUPPORT OF A MEMBRANE FILTER IN A MEDICAL INFUSION SYSTEM

(75) Inventor: Ernest Balestracci, Iselin, NJ (US)

(73) Assignee: Bracco Diagnostics, Inc., Princeton, NJ (US)

( * ) Notice: Subject to any disclaimer, the term of this patent is extended or adjusted under 35 U.S.C. 154(b) by 270 days.

(21) Appl. No.: 12/273,899

(22) Filed: Nov. 19, 2008

(65) Prior Publication Data

US 2010/0125243 A1 May 20, 2010

(51) Int. Cl.
*A61M 31/00* (2006.01)

(52) U.S. Cl. .................................................. 604/93.01

(58) Field of Classification Search ............... 29/525.01; 604/93.01, 118; 210/321.6; D8/394; 292/338, 292/236.75, 256
See application file for complete search history.

(56) References Cited

U.S. PATENT DOCUMENTS

| | | | |
|---|---|---|---|
| 3,483,867 A | 12/1969 | Markovitz | |
| 3,710,118 A | 1/1973 | Holgate | |
| 3,714,429 A | 1/1973 | Mozley | |
| 3,774,036 A | 11/1973 | Gerhart | |
| 3,997,784 A | 12/1976 | Pecunko | |
| 4,096,859 A | 6/1978 | Agarwal | |
| 4,286,169 A | 8/1981 | Rossem | |
| 4,336,036 A | 6/1982 | Leeke et al. | |
| 4,466,888 A | 8/1984 | Verkaart | |
| 4,562,829 A | 1/1986 | Bergner | |
| 4,585,009 A | 4/1986 | Barker | |
| 4,585,941 A | 4/1986 | Bergner | |
| 4,623,102 A * | 11/1986 | Hough, Jr. | 248/68.1 |
| 4,625,118 A | 11/1986 | Kriwetz | |
| 4,679,142 A | 7/1987 | Lee | |
| 4,755,679 A | 7/1988 | Wong | |
| 4,769,008 A | 9/1988 | Hessel | |
| 4,853,546 A | 8/1989 | Abe | |
| 4,994,056 A * | 2/1991 | Ikeda | 604/410 |
| 5,039,863 A | 8/1991 | Matsuno | |
| 5,258,906 A | 11/1993 | Kroll | |
| 5,274,239 A | 12/1993 | Lane | |

(Continued)

FOREIGN PATENT DOCUMENTS

EP 0102121 3/1984

(Continued)

OTHER PUBLICATIONS

International Search Report and Written Opinion, dated Jan. 4, 2010 for PCT Application No. PCT/US2009/063788, 13 pages.

(Continued)

*Primary Examiner* — Jackie Ho
*Assistant Examiner* — Weng Lee
(74) *Attorney, Agent, or Firm* — Fredrikson & Byron, PA

(57) ABSTRACT

A removable clamp, for supporting a membrane filter in a medical infusion system, includes connected and opposing walls. A locking feature, which may be connected to an end of one of the walls, engages and disengages a terminal end of the other wall. The filter may be inserted between the opposing walls of the clamp, and an inner surface of each of the opposing walls may be secured against corresponding major surfaces of the inserted filter, by only pressing at least one of the opposing walls of the clamp toward the other of the opposing walls.

4 Claims, 5 Drawing Sheets

U.S. PATENT DOCUMENTS

| | | | |
|---|---|---|---|
| 5,475,232 | A | 12/1995 | Powers |
| 5,485,831 | A | 1/1996 | Holdsworth |
| 5,590,648 | A | 1/1997 | Mitchell |
| 5,702,115 | A | 12/1997 | Pool |
| 5,739,508 | A | 4/1998 | Uber, III |
| 5,765,842 | A | 6/1998 | Phaneuf |
| 5,827,429 | A | 10/1998 | Ruschke et al. |
| 5,840,026 | A | 11/1998 | Uber, III |
| 5,885,216 | A | 3/1999 | Evans, III |
| 6,157,036 | A | 12/2000 | Whiting |
| 6,347,711 | B1 | 2/2002 | Goebel et al. |
| 6,442,418 | B1 | 8/2002 | Evans, III |
| 6,558,125 | B1 * | 5/2003 | Futterknecht ............ 417/1 |
| 6,626,862 | B1 | 9/2003 | Duchon |
| 6,767,319 | B2 | 7/2004 | Reilly |
| 6,870,175 | B2 | 3/2005 | Dell |
| 6,901,283 | B2 | 5/2005 | Evans, III |
| 6,908,598 | B2 | 6/2005 | Sylvester |
| 7,163,031 | B2 | 1/2007 | Graves |
| 7,169,135 | B2 | 1/2007 | Duchon |
| 7,204,797 | B2 | 4/2007 | Reilly |
| 7,256,888 | B2 | 8/2007 | Staehr |
| 7,413,123 | B2 | 8/2008 | Ortenzi |
| 7,476,377 | B2 | 1/2009 | Moller |
| 7,504,646 | B2 | 3/2009 | Balestracci |
| 7,612,999 | B2 | 11/2009 | Clark |
| 7,862,534 | B2 | 1/2011 | Quirico |
| 2004/0104160 | A1 * | 6/2004 | Scagliarini et al. ...... 210/321.75 |
| 2005/0278066 | A1 | 12/2005 | Graves |
| 2006/0015056 | A1 | 1/2006 | Ellingboe |
| 2006/0151048 | A1 | 7/2006 | Tochon-Danguy |
| 2007/0140958 | A1 | 6/2007 | DeKemp |
| 2007/0213848 | A1 | 9/2007 | DeKemp |
| 2007/0232980 | A1 | 10/2007 | Felt |
| 2007/0282263 | A1 | 12/2007 | Kalafut |
| 2008/0071219 | A1 | 3/2008 | Rhinehart |
| 2008/0093564 | A1 | 4/2008 | Tartaglia |
| 2008/0166292 | A1 | 7/2008 | Levin |
| 2008/0242915 | A1 | 10/2008 | Jackson |
| 2009/0309466 | A1 | 12/2009 | Quirico |
| 2009/0312630 | A1 | 12/2009 | Hidem |
| 2009/0312635 | A1 | 12/2009 | Shimchuk |
| 2009/0318745 | A1 | 12/2009 | Quirico |
| 2010/0270226 | A1 | 10/2010 | Balestracci |
| 2010/0312039 | A1 | 12/2010 | Quirico |
| 2011/0071392 | A1 | 3/2011 | Quirico |
| 2011/0172524 | A1 | 7/2011 | Hidem |

FOREIGN PATENT DOCUMENTS

| | | | |
|---|---|---|---|
| EP | 0160303 | | 11/1985 |
| EP | 0310148 | | 4/1989 |
| EP | 0919249 | A1 | 6/1999 |
| EP | 1421960 | A1 | 5/2004 |
| FR | 2867084 | | 9/2005 |
| JP | 2000350783 | | 12/2000 |
| JP | 2006325826 | | 12/2006 |
| WO | 9615337 | | 5/1996 |
| WO | 9956117 | | 11/1999 |
| WO | 02096335 | | 12/2002 |
| WO | 2004059661 | | 7/2004 |
| WO | 2005002971 | | 1/2005 |
| WO | 2006007750 | | 1/2006 |
| WO | 2006026603 | | 3/2006 |
| WO | 2006074473 | | 7/2006 |
| WO | 2006129301 | | 12/2006 |
| WO | 2006135374 | | 12/2006 |
| WO | 2007016170 | | 2/2007 |
| WO | 2007030249 | | 3/2007 |
| WO | 2007071022 | | 6/2007 |
| WO | 2007104133 | | 9/2007 |
| WO | 2007149108 | | 12/2007 |
| WO | 2008028165 | | 3/2008 |
| WO | 2008037939 | | 4/2008 |
| WO | 2008082966 | | 7/2008 |
| WO | 2008140351 | | 11/2008 |
| WO | 2009152320 | A2 | 12/2009 |
| WO | 2010020596 | | 2/2010 |

OTHER PUBLICATIONS

Brochure, "IV and Liquid Filters: Speedflow Adult 0.2 um Positive", http://www.gvs.it/flex/FixedPages/UK/LiquidFilters.php/L/UK/ID/Speedflow%20Adjust%....taken off of web on Nov. 11, 2008.

Bracco Brochure, "Rubidium 82 Infusion System, Easy to Operate . . . Automated . . . Complete", © Bracco Diagnostics, Inc., 0605-002NA, Jun. 2001. (2 pages).

Bracco, "Cardio-Gen82® Infusion System User's Guide", pp. 1-42.

Imaging Technology News, web exclusive: "FDG-PET Injector Thrusts New Life into Molecular Imaging", Apr. 2008, 2 pages.

Neil J. Epstein, et al., "A Rb82 infusion system for quantitative perfusion imaging with 3D PET" Applied Radiation and Isotopes, vol. 60, Feb. 9, 2004, pp. 921-927, XP002557544 DOI:10, 1016/j.apradiso.2004.02.002.

R. Klein, et al., "Precision controlled elution of a Sr82/Rb82 generator for cardiac perfusion imaging with positron emission tomography" Physics in Medicine and Biology, vol. 52, Jan. 11, 2007, pp. 659-673, XP002557545 DOI:10, 1088/0031-9155/52/3/009.

International Search Report and Written Opinion, dated Feb. 25, 2010 for PCT Application No. PCT/US2009/047027, 22 pages.

International Search Report and Written Opinion, dated Feb. 17, 2010 for PCT Application No. PCT/US2009/047030, 17 pages.

International Search Report and Written Opinion, dated Mar. 1, 2010 for PCT Application No. PCT/US2009/047031, 20 pages.

International Search Report and Written Opinion, dated Feb. 25, 2010 for PCT Application No. PCT/US2009/047034, 15 pages.

* cited by examiner

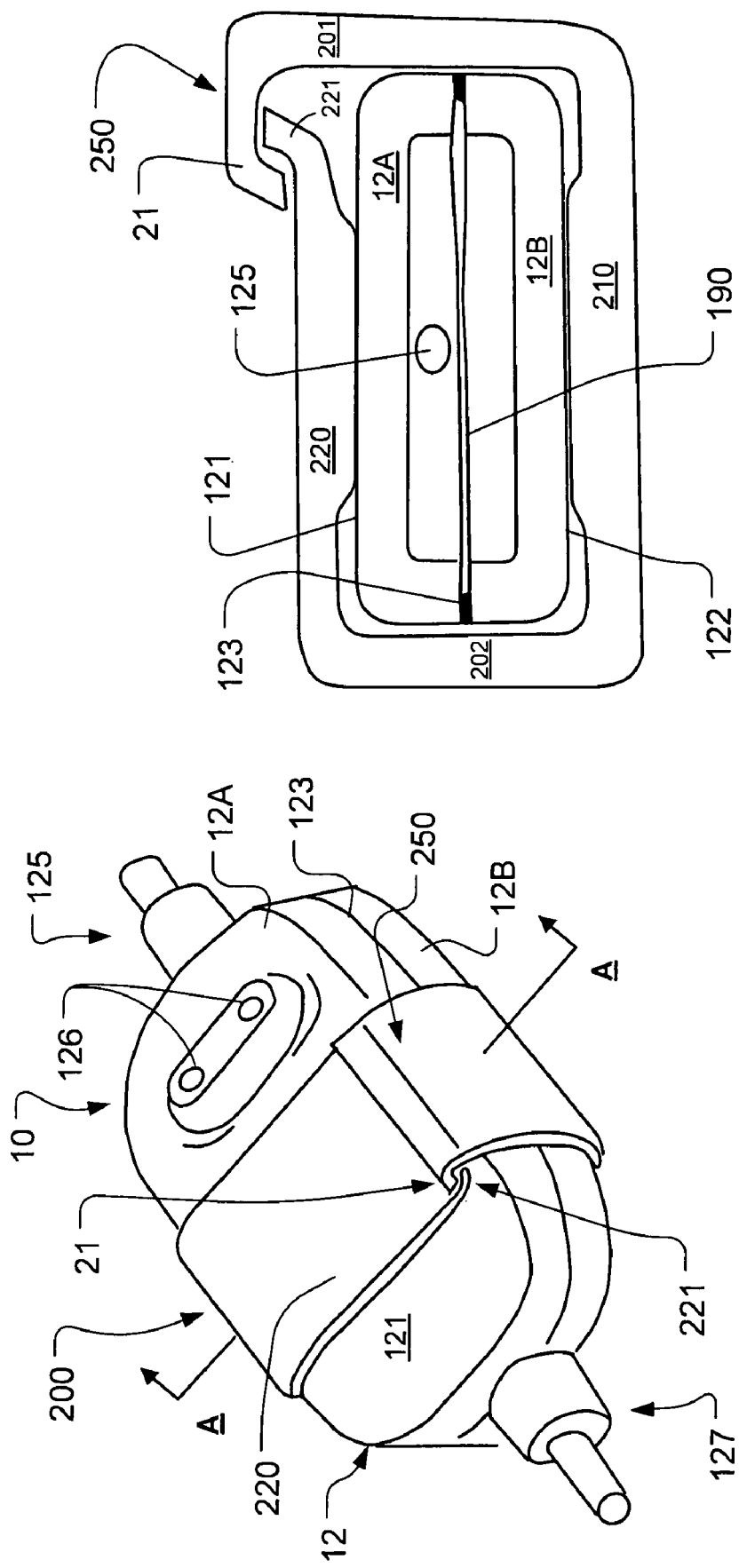

APPARATUS AND METHODS FOR SUPPORT OF A MEMBRANE FILTER IN A MEDICAL INFUSION SYSTEM

TECHNICAL FIELD

The present invention pertains to medical infusion systems and more particularly to the support of membrane filters incorporated therein.

BACKGROUND

Fluid circuits of medical infusion systems typically include at least one filter to assure that air, and/or other gases, are not introduced, for example, into a venous system of a patient, along with the infused fluid. The membrane-type filter includes a hydrophilic membrane, which extends between an inlet and an outlet of the filter, and a hydrophobic membrane which extends between the inlet and vent holes of the filter. The hydrophilic membrane is fluid permeable, yet gas impermeable, and the hydrophobic membrane is fluid impermeable, yet gas permeable. The design and operation of these membrane-type filters are known to those skilled in the art. One such filter is the Speedflow Adult 0.2 μm Positive, which is available from GVS Group (headquartered in Bologna, Italy).

Membrane filters are typically constructed for relatively low pressure applications (i.e. less than approximately 3.5 bar or approximately 50 psi), and to be relatively inexpensive, flexible and disposable. Thus, the housings of these filters may be susceptible to failure, if the filters are employed by infusion systems that inject fluids at higher pressures. Support for the housings of these filters has been proposed, yet, there is still a need for new apparatus and methods for supporting membrane filters.

BRIEF DESCRIPTION OF THE DRAWINGS

The following drawings include those illustrative of particular embodiments of the present invention, and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 3A is a perspective view of the filter of FIG. 1A secured within the clamp of FIG. 2, according to some embodiments.

FIG. 3B is a cross-section view through section line A-A of FIG. 3A, according to some embodiments.

DETAILED DESCRIPTION

The following detailed description is exemplary in nature and is not intended to limit the scope, applicability, or configuration of the invention in any way. Rather, the following description provides practical illustrations for implementing exemplary embodiments. Utilizing the teaching provided herein, those skilled in the art will recognize that many of the examples have suitable alternatives that can be utilized.

Figures 1A, 1B:
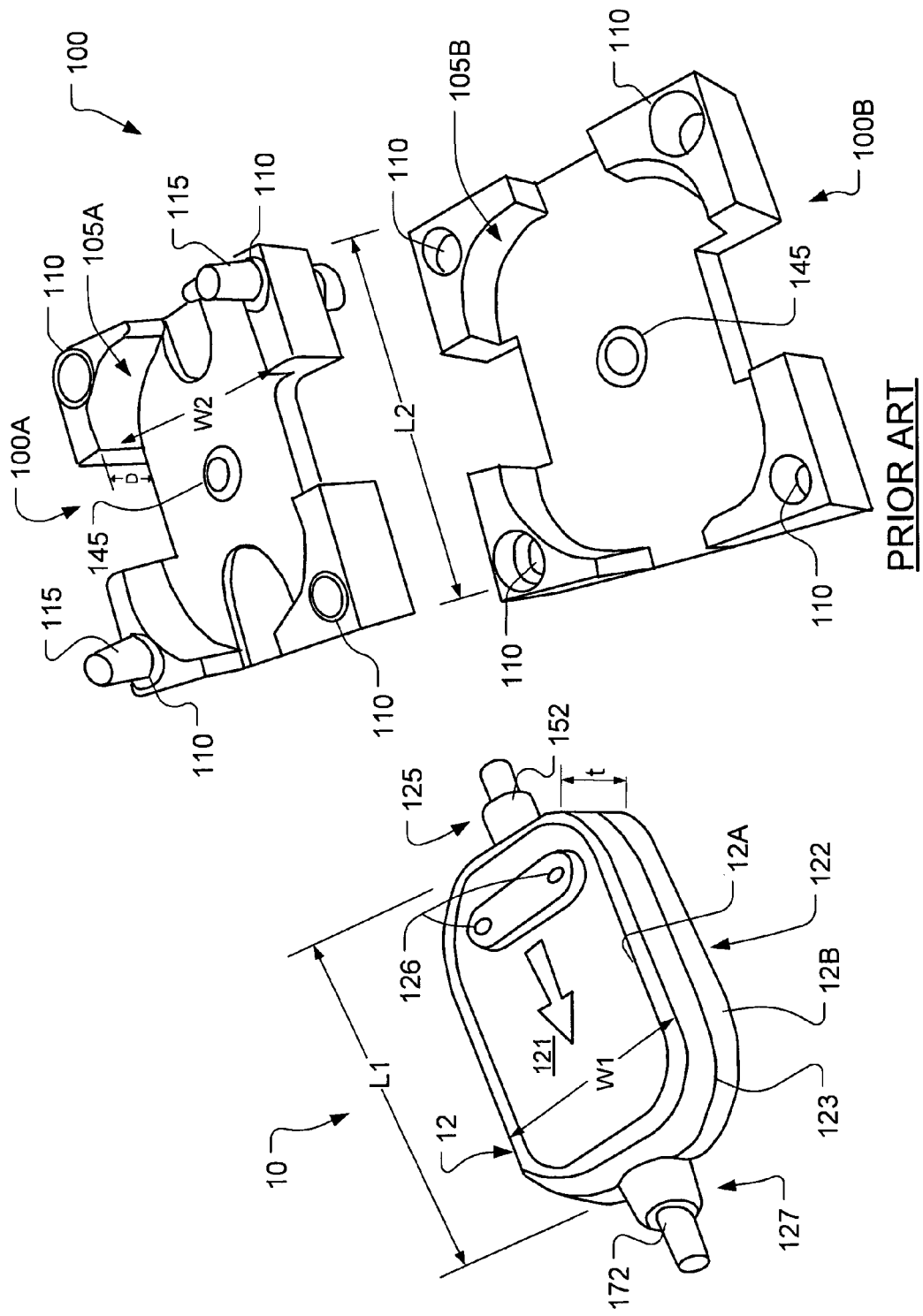
FIG. 1A is a perspective view of an exemplary membrane filter.
FIG. 1B is a perspective view of an exemplary prior art auxiliary housing for the filter shown in FIG. 1A.

FIG. 1A is a perspective view of an exemplary membrane filter 10, which is very similar to the aforementioned filter supplied by GVS Group. FIG. 1A illustrates filter 10 including a housing 12, an inlet 125 and an outlet 127; a first fitting 152, for example, a female Luer lock, is shown joined to inlet 125, and a second fitting 172, for example, a rotating male Luer lock, is shown joined to outlet 127. FIG. 1A further illustrates housing 12 including a first sidewall 12A, a second sidewall 12B and a perimeter seam 123 at which first and second sidewalls 12A, 12B are joined together, for example, via adhesive bonding or ultrasonic welding; vent holes 126 are shown formed through a protruding portion of first sidewall 12A, in proximity to inlet 125. Those skilled in the art will appreciate that a hydrophilic membrane 190, which may be captured between sidewalls 12A, 12B, at seam 123 (FIG. 3B), extends within housing to divide housing into an inlet compartment, in proximity to inlet 125, and an outlet compartment, in proximity to outlet 127; and, further, that a hydrophobic membrane, for example, being attached to first sidewall 12A, extends between the inlet compartment and vent holes 126. When filter 10 is connected, via fittings 152, 172, into a fluid circuit of a medical infusion system, the joint at seam 123 should be able to withstand the pressures of injection fluid flow through filter 10, otherwise first and second sidewalls 12A, 12B of housing 12 will separate from one another, thereby causing a failure of the system.

FIG. 1B is a perspective view of an exemplary prior art auxiliary housing 100, which is very similar to an auxiliary housing provided by GVS group for support of a filter that is similar to filter 10. FIG. 1B illustrates housing 100 including a first part 100A and a second part 10B; each of first and second parts 100A, 100B include a cavity 105A and 105B, respectively, to surround and support housing 12 of filter 10 when auxiliary housing 100 is assembled around filter 10. In order to assemble housing 100 around filter 10, first and second parts 100A, 100B must be fastened together around filter 10. FIG. 1B further illustrates each part 100A, 100B including securing features 110 formed therein, and fasteners 115, for example, thumb screws, inserted into two of securing features 110 in first part 100A. In order to fasten parts 100A, 100B together around filter 10, cavities 105A, 105B of parts 10A, 100B must be aligned with filter housing 12, and securing features 110 of first part 100A also aligned with corresponding securing features 110 of second part 10B; then, fasteners 115 must be mated with the aligned features 110.

With reference back to FIG. 1A, in conjunction with FIG. 1B, it may be appreciated that a length L1 and a width W1 of housing 12 are either less than or equal to a length L2 and a width W2, respectively, of cavities 105A, 105B, so that when auxiliary housing 100 is assembled around filter 10, filter housing 12 will be completely enclosed within cavities 105A, 105B. Furthermore, a depth D of each cavity 105A, 105B, in conjunction with adjustment of fasteners 115, is such that first and second parts 10A, 10B, when fastened together around filter housing 12, may restrain sidewalls 12A, 12B from separating at seam 123, under higher operating pressures. Each part 10A, 100B is shown including a feature 145, which protrudes into the respective cavity 105A, 105B, in order to directly interface with each of sidewalls 12A, 12B, when first and second parts 100A, 100B are fastened together around filter 10; at least one of features 145 may be movable to adjust a pressure at the interface with the corresponding sidewall 12A, 12B.

With further reference to FIG. 1B, it may be appreciated that the design of auxiliary housing 100 has several drawbacks, for example, related to the bulk and the handling thereof. In particular, a size of auxiliary housing 100 is such that vent holes 126 may be blocked by one of first and second parts 100A, 100B, when assembled around housing 12, thereby potentially compromising the function of filter 10; and, with respect to handling, the aforementioned steps, which are necessary to assemble auxiliary housing 100 around filter 10, are relatively numerous and tedious.

Figure 2:
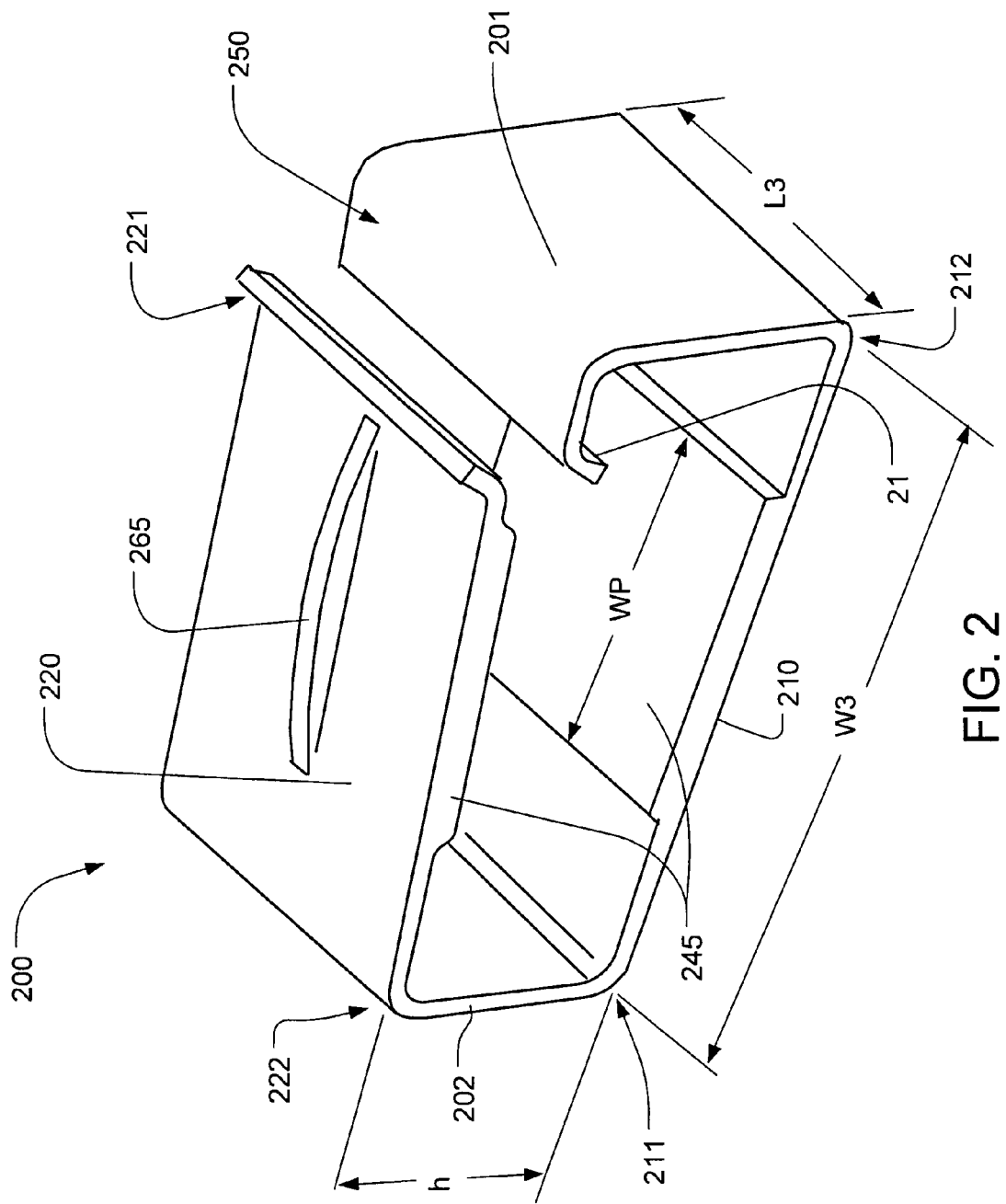
FIG. 2 is a perspective view of a removable clamp, according to some embodiments of the present invention.

FIG. 2 is a perspective view of a removable clamp 200, according to some embodiments of the present invention. FIG. 2 illustrates clamp 200 including a first support wall 210, which extends from a first end 211 thereof to a second end 212 thereof, a locking feature 250, which is connected to second end 212, and a second support wall 220, opposite first support wall 210, which extends from a first, terminal end 221 thereof to a second end 222 thereof. FIG. 2 further illustrates locking feature 250 being formed by a first sidewall 201, which extends from second end 212 of first support wall 210; first sidewall 201 is shown extending toward second support wall 220 and including a terminal portion 21 that bends toward first support wall 210.

According to the illustrated embodiment, first, terminal end 221 of second support wall 220 bends away from first support wall 210, such that first, terminal end 221 can interlock with terminal portion 21 of first sidewall 201, when second support wall 220 is deflected toward first support wall 210. FIG. 2 further illustrates second end 222 of second support wall 220 being flexibly connected to first end 211 of first support wall 210 by a second sidewall 202, which extends opposite first sidewall 201, and allows for the deflection of second support wall 220. According to preferred embodiments, clamp 200 is an injection molded plastic part, such that each of walls 210, 201, 220, 202 are integrally formed. Clamp 200 is preferably formed from a polycarbonate resin, for a suitable combination of flexibility and strength; yet, those skilled in the art will appreciate that other plastic materials, which demonstrate similar flexibility and strength, may alternatively be employed. With reference to FIGS. 1A and 2, according to an exemplary embodiment, when width W1 of filter 10 is approximately 1.14 inches, and a thickness t of filter 10 is approximately 0.356 inch, a width W3 of first support wall 210 is approximately 1.25 inches, and a height h of second sidewall 202 is approximately 0.375 inch.

According to the illustrated embodiment, after filter 10 is inserted between support walls 210 and 220 of clamp 200, first, terminal end 221 of second support wall 220 may be engaged by locking feature 250, by simply pressing second support wall 220 toward first support wall 210. FIG. 3A is a perspective view of filter 10 supported by clamp 200; and FIG. 3B is a cross-section view through section line A-A of FIG. 3A, according to some embodiments. FIGS. 3A-B illustrate first, terminal end 221 of support wall 220 interlocking with terminal portion 21 of sidewall 201, in order to secure an inner surface of second support wall 220 against a first major surface 121 of filter sidewall 12A, and an inner surface of first support wall 210 against a second major surface 122 of filter sidewall 12B. Thus, clamp 200 supports housing 12 of inserted filter 10 against pressures that result from fluid flow through filter 10, which may otherwise cause the joint, which connects first sidewall 12A to second sidewall 12B, at seam 123, to fail.

FIGS. 2 and 3B illustrate each of first and second support walls 210, 220 including an optional inward projecting plateau 245, which forms the corresponding inner surfaces of walls 210, 220; a width WP of each plateau 245 (FIG. 2) may be approximately 0.625 inch, when width W1 of filter 10 is approximately 1.14 inches. According to some preferred embodiments, the inner surfaces formed by plateaus 245 are spaced apart from one another at a distance that is less than a thickness t (FIG. 1A) of filter 10, when locking feature 250 engages first, terminal end 221 of second support wall 220 to support housing 12; this spacing may be between approximately 0.02 inch and approximately 0.05 inch less than thickness t. FIG. 2 further illustrates second support wall 220 including an optional, outwardly projecting, strengthening feature 265, in the form of a rib.

With further reference to FIG. 3A, it can be seen that no portion of clamp 200 extends over vent holes 126 of filter 10, when clamp 200 supports housing 12 of filter 10. According to an exemplary embodiment, when length L1 of filter 10 (FIG. 1A) is approximately 1.575 inches, a length L3 of clamp 200 (FIG. 2) is approximately 0.625 inch.

Figure 4A:
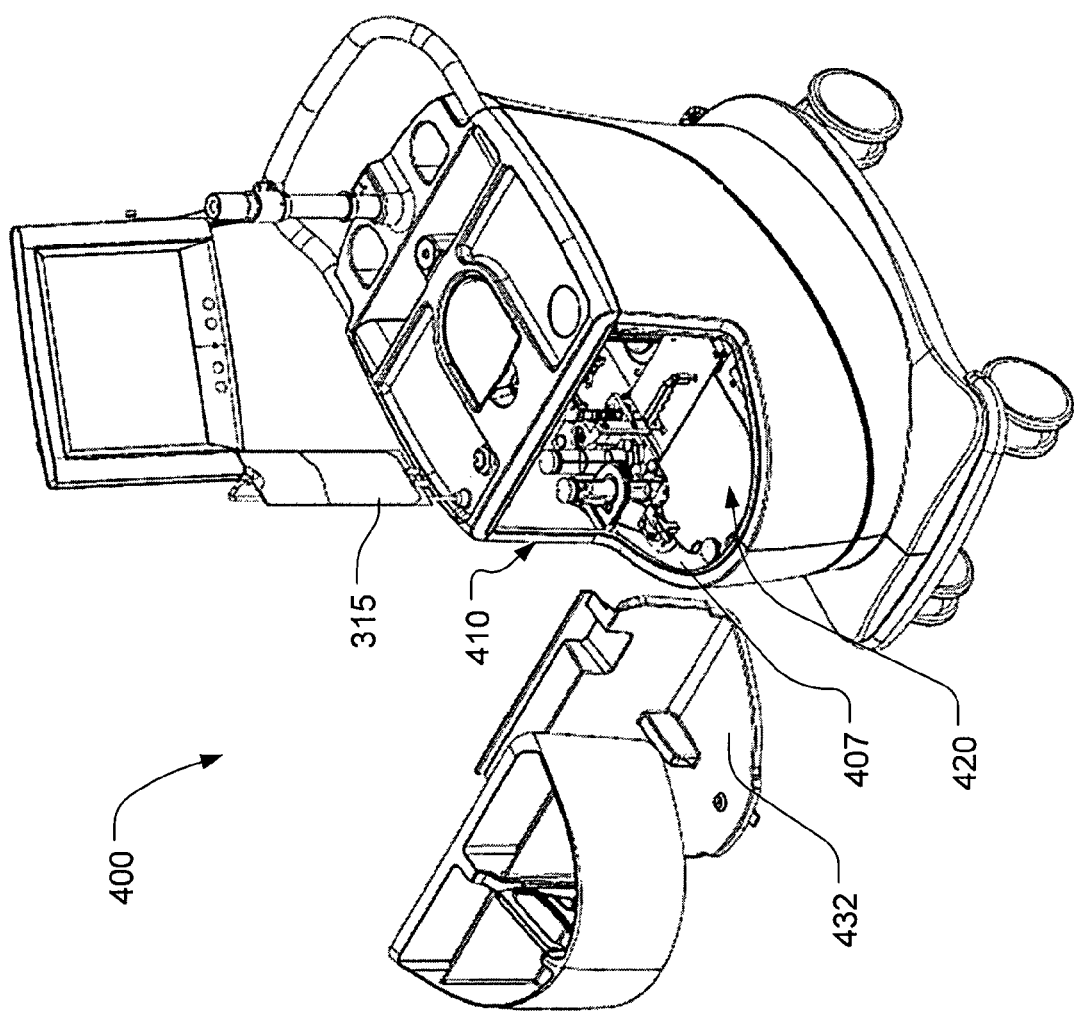
FIG. 4A is a perspective view of an exemplary infusion system.
Figure 4B:
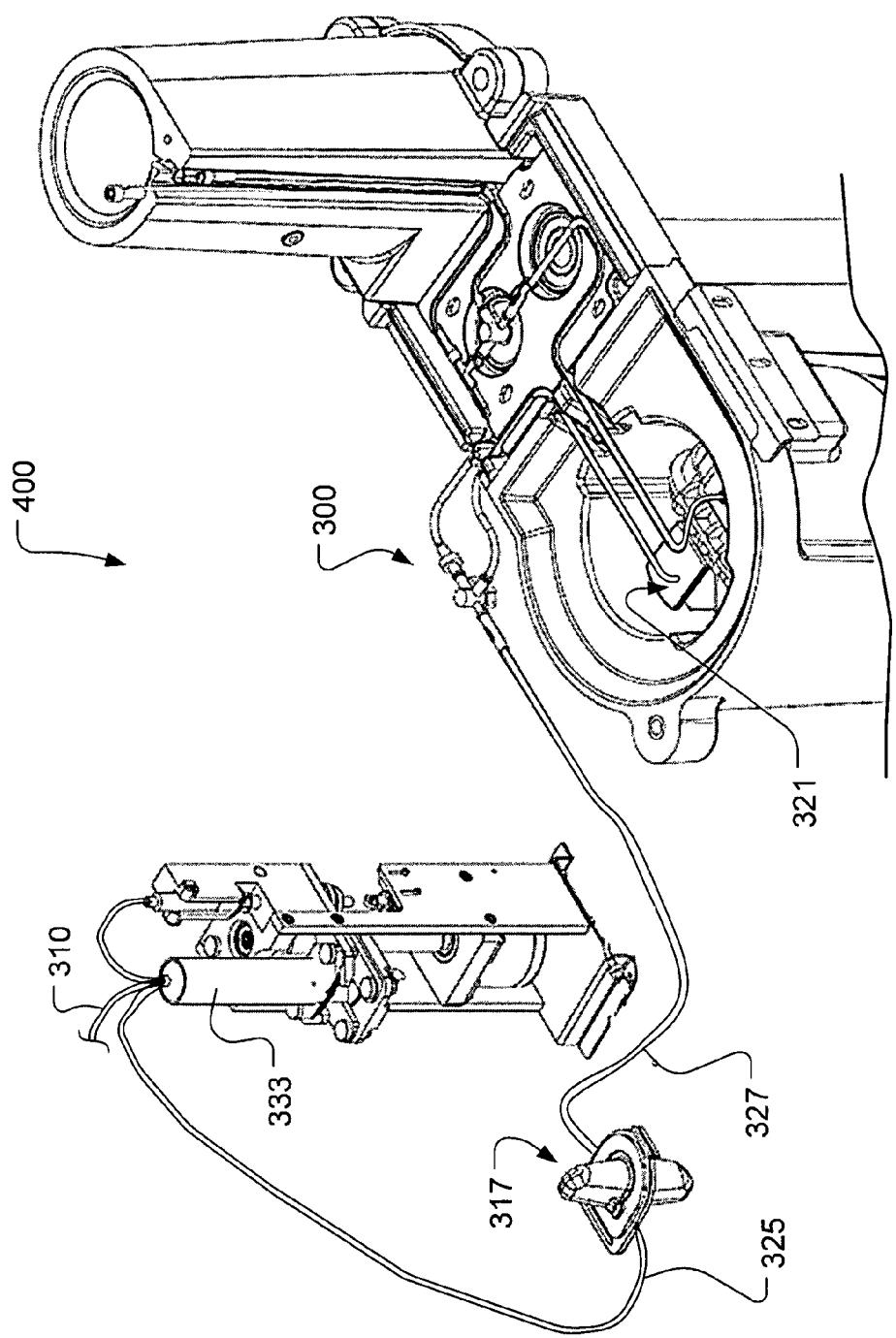
FIG. 4B is a perspective view of a portion of the infusion system, shown in FIG. 4A, which may incorporate embodiments of the present invention.

Turning now to FIGS. 4A-B an exemplary medical infusion system, in which embodiments of the present invention may be employed, will now be briefly described. FIG. 4A is a perspective view of a radiopharmaceutical infusion system 400; and FIG. 4B is a perspective view of a portion of infusion system 400 that includes a fluid circuit 300. FIG. 4A illustrates infusion system 400 including a cabinet 410, in which a portion of fluid circuit 300 is enclosed, and which includes an access panel 432 by which enclosed fluid circuit 300 may be accessed for maintenance thereof. A shielding assembly 420 is also shown enclosed within cabinet 410 in order to shield radioactive segments of fluid circuit 300. Infusion system 400 may be used for medical diagnostic imaging, for example, Positron Emission Tomography (PET), wherein doses of radiopharmaceutical, which are generated by elution within a radioisotope generator 321 (FIG. 4B), are injected, or infused into a patient. The infused dose of radiopharmaceutical is absorbed by cells of a target organ, of the patient, and emits radiation, which is detected by a PET scanner, in order to generate an image of the organ. An example of a radioactive isotope, which may be used for PET, is Rubidium-82 (produced by the decay of Strontium-82); and an example of a radioisotope generator, which yields a saline solution of Rubidium-82, via elution, is the CardioGen-82® available from Bracco Diagnostics Inc. (Princeton, N.J.). Embodiments of such an infusion system 400 are described in co-pending an commonly assigned U.S. patent application Ser. No. 12/137,363, which is hereby incorporated by reference.

FIG. 4A illustrates a reservoir 315 of fluid circuit 300, which is mounted outside cabinet 410, and FIG. 4B illustrates a pump 333 of fluid circuit 300, which is located within cabinet 410 and is supplied by reservoir 315, via a tubing line 310 that extends through a sidewall of cabinet 410. According to FIGS. 4A-B, pump 333 provides a pressure pulse to drive infusion injections, first through a filter, via an input tubing line 325, and then through the remainder of tubing circuit 300, via an output tubing line 327. In order to assure quality diagnostic imaging, pressure pulses of between approximately 75 psi and approximately 125 psi are typically applied to inject doses, or boluses, of the radiopharmaceuticals, that are generated by system 400. Thus, those elements of fluid circuit 300, which are downstream of pump 333, must be able to withstand pressure pulses of up to, and possibly exceeding, approximately 125 psi. Furthermore, these elements of fluid circuit 300 are typically required to function for as many as 310 to 325 injection pulses, at these pressures.

According to some embodiments of the present invention, fluid circuit 300 of infusion system 400 incorporates filter 10, which is supported by clamp 200, for example, as is illustrated in FIGS. 3A-B. When inner surfaces of opposing support walls 210, 220 of clamp 200 are secured against surfaces 121, 122 of filter housing 12, as previously described, clamp 200 may prevent separation of housing sidewalls 12A, 12B at seam 123 when loaded under the aforementioned pressure pulses. With reference to FIG. 4B, input tubing line 325 may be connected to first fitting 152, at inlet 125 of filter 10, and output tubing line 327 to second fitting 172, at outlet 127 of filter 10. According to exemplary embodiments of system 400, filter 10 is the aforementioned Speedflow Adult 0.2 μm Positive (GVS Group), and filter 10 and clamp 200 are each of a size defined by the corresponding and exemplary length, width, thickness and height dimensions set forth herein, above.

Filter 10, being supported by clamp 200, may be directly mounted within cabinet 410 of infusion system 400, for example, along an inside wall 407 thereof (FIG. 4A). Alternatively, FIG. 4B illustrates infusion system 400 including a holder 317 for filter 10 and clamp 200. Holder 317 may be formed from a thermoformed plastic sheet into a clam-shell structure, which encloses filter 10 and clamp 200 in an interior space, and allows inlet and outlet tubing lines 325, 327 to extend out from the interior space, in between opposing sides thereof. Holder 317 may be hung from a structure (not shown) along inside wall 407.

According to some methods of the present invention, in order to assemble filter 10 into fluid circuit 300, such that the filter can withstand the aforementioned pressure pulses without failure, filter 10 is first inserted between opposing support walls 210, 220 of clamp 200, either before or after connecting one or both of inlet and outlet fittings 152, 172 to inlet and outlet tubing lines 325, 327, respectively. After filter 10 is inserted, the one assembling circuit 300, need only press second support wall 220 toward first support wall 210, or visa versa, in order to engage first, terminal end 221 of second support wall 220 with locking feature 250 of clamp 200, thereby securing inner surfaces of support walls 210, 220 against corresponding surfaces 121, 122 of filter 10. This securing step may be performed either before or after connecting inlet and outlet fittings 152, 172 of filter 10 to corresponding tubing lines 325, 327. When circuit 300 is disassembled, after a predetermined life, clamp 200 may be removed from filter 10, for example, by deflecting first and second sidewalls 201, 202 away from one another to release first, terminal end 221 of support wall 220 from the interlock with terminal portion 21 of first sidewall 201, so that clamp 200 may be re-used to support another filter.

In the foregoing detailed description, the invention has been described with reference to specific embodiments. However, it may be appreciated that various modifications and changes can be made without departing from the scope of the invention as set forth in the appended claims.

I claim:

1. A medical infusion system for injecting radiopharmaceuticals into a patient, the infusion system including a fluid circuit through which pressure pulses of between approximately 75 psi and 125 psi are applied, and a cabinet in which at least a portion of the fluid circuit is enclosed, the fluid circuit including a membrane filter, the filter including a housing, a fluid inlet and a fluid outlet, the fluid inlet being connected to a fluid inlet line of the circuit, the fluid outlet being connected to a fluid outlet line of the circuit, the housing of the filter having a length that extends between the fluid inlet and the fluid outlet of the filter, a width that extends approximately orthogonal to the length, and a thickness, and the housing including a first sidewall, through which vent holes are formed in proximity to the fluid inlet, and a second sidewall joined to the first sidewall at a perimeter seam of the housing, the first sidewall having a first major surface and the second sidewall having a second major surface opposite the first major surface, the first and second major surfaces extending on either side of the seam, and the thickness of the housing being defined from the first major surface to the second major surface, at a location around a common perimeter of the surfaces, and being less than the length and the width of the housing; and wherein the system further comprises:

a removable clamp assembled about the housing of the membrane filter to support the housing, without extending over the vent holes of the filter, in order to restrain the first and second sidewalls of the filter from separating from one another under the applied pressure pulses, the removable clamp and the filter being mounted within the cabinet; and the clamp comprising:

a first support wall including a first end, a second end, opposite the first end, and an inner surface formed by a first inward projecting plateau, the first support wall having a width, defined from the first end thereof to the second end thereof, the width of the first support wall spanning the width of the housing of the filter, and the first plateau having a width that extends approximately orthogonal to the length of the housing and is less than the width of the housing but greater than approximately one half the width of the housing;

a second support wall, opposite the first support wall, including a first, terminal end, a second end, opposite the first, terminal end, and an inner surface formed by a second inward projecting plateau, the second end of the second support wall being fixedly and flexibly connected to the first end of the first support wall to allow the first, terminal end of the second support wall to move toward and away from the first support wall, and the second plateau having a width that extends approximately orthogonal to the length of the housing and is less than the width of the housing but greater than approximately one half the width of the housing; and a locking feature connected to the second end of the first support wall and being configured to engage and disengage the first, terminal end of the second support wall, the locking feature engaging the first terminal end of the second support wall of the assembled clamp, such that the inner surface formed by the first plateau is secured against one of the first and second major surfaces of the housing and the inner surface formed by the second plateau is secured against the other of the first and second major surfaces of the housing, directly opposite the inner surface of the first plateau;

wherein the first support wall, in proximity to the first end thereof, is spaced apart from the second support wall, in proximity to the second end thereof, over a distance that spans the thickness of the housing; and the clamp is removable from around the housing when the locking feature disengages the first, terminal end of the second support wall.

2. The infusion system of claim 1, further comprising a holder for the membrane filter and the removable clamp, assembled thereabout; and wherein the cabinet includes an internal feature on which to hang the holder.

3. The infusion system of claim 1, wherein at least one of the first and second support walls of the removable clamp has an overall length, defined in a direction approximately orthogonal to the width of the first support wall, and the overall length is less than the length of the housing of the filter.

4. The infusion system of claim 1, wherein:
the locking feature of the removable clamp is formed by a sidewall thereof extending from the second end of the first support wall of the clamp to a terminal portion thereof, the terminal portion bending toward the first support wall of the clamp; and
the first, terminal end of the second support wall of the removable clamp bends away from the first support wall of the clamp, such that the first, terminal end interlocks with the terminal portion of the sidewall of the clamp, when the locking feature of the clamp engages the first, terminal end.

\* \* \* \* \*